(12) United States Patent
Costa et al.

(10) Patent No.: US 10,987,305 B2
(45) Date of Patent: Apr. 27, 2021

(54) PREPARATION OF RESPIRABLE ZAFIRLUKAST PARTICLES

(71) Applicant: Hovione Scientia Limited, Cork (IE)

(72) Inventors: Eunice Costa, Lisbon (PT); Susana Campos, Al Paio Pires (PT); Filipe Neves, Lisbon (PT)

(73) Assignee: Cipla Limited, Mumbai (IN)

( * ) Notice: Subject to any disclaimer, the term of this patent is extended or adjusted under 35 U.S.C. 154(b) by 178 days.

(21) Appl. No.: 16/062,766

(22) PCT Filed: Dec. 15, 2016

(86) PCT No.: PCT/GB2016/053953
§ 371 (c)(1),
(2) Date: Jun. 15, 2018

(87) PCT Pub. No.: WO2017/103600
PCT Pub. Date: Jun. 22, 2017

(65) Prior Publication Data
US 2019/0282543 A1    Sep. 19, 2019

(30) Foreign Application Priority Data

Dec. 15, 2015 (PT) ........................................ 109030

(51) Int. Cl.
*A61K 9/00* (2006.01)
*A61K 9/16* (2006.01)
(Continued)

(52) U.S. Cl.
CPC .......... *A61K 9/0075* (2013.01); *A61K 9/1623* (2013.01); *A61K 9/1682* (2013.01);
(Continued)

(58) Field of Classification Search
None
See application file for complete search history.

(56) References Cited

U.S. PATENT DOCUMENTS 5,319,097 A   6/1994   Holohan et al.
5,482,963 A   1/1996   Holohan et al.
(Continued)

FOREIGN PATENT DOCUMENTS

JP   H04266872 A    9/1992
JP   2005508220 A   3/2005
(Continued)

OTHER PUBLICATIONS

Foreign Communication from a related application—International Search Report and Written Opinion of International Application No. PCT/GB2016/053953 dated Mar. 7, 2017, 10 pages.
(Continued)

*Primary Examiner* — Robert A Wax
*Assistant Examiner* — Quanglong N Truong
(74) *Attorney, Agent, or Firm* — Conley Rose, P.C.; Rodney B. Carroll (57) ABSTRACT

A method for the preparation of respirable zafirlukast monohydrate particles comprises the steps of preparation of an aqueous suspension of amorphous zafirlukast; size-reduction with conversion of the suspended zafirlukast into crystalline monohydrate nanoparticles; and isolation of the crystalline zafirlukast in the form of a dry powder. Also provided are zafirlukast respirable particles characterized by comprising crystalline monohydrate zafirlukast. Pharmaceutical compositions comprising the particles are also disclosed, as is the use of the particles or compositions for the treatment of respiratory diseases.

26 Claims, 4 Drawing Sheets

(51) Int. Cl.
  *A61K 9/19* (2006.01)
  *A61K 31/404* (2006.01)
  *A61K 47/26* (2006.01)
  *A61K 47/18* (2017.01)

(52) U.S. Cl.
  CPC .............. *A61K 9/19* (2013.01); *A61K 31/404* (2013.01); *A61K 47/183* (2013.01); *A61K 47/26* (2013.01)

(56) References Cited

U.S. PATENT DOCUMENTS

| | | | |
|---|---|---|---|
| 5,504,216 A | 4/1996 | Holohan et al. | |
| 5,612,367 A | 3/1997 | Timko et al. | |
| 5,993,859 A | 11/1999 | Timko et al. | |
| 6,143,775 A | 11/2000 | Holohan et al. | |
| 6,224,907 B1 * | 5/2001 | Davar ................. | A61K 31/381 424/473 |
| 2004/0058901 A1 | 3/2004 | Gutman et al. | |
| 2005/0101544 A1 | 5/2005 | Robinson et al. | |
| 2005/0113410 A1 * | 5/2005 | Tawa ..................... | A61K 31/47 514/311 |
| 2005/0244340 A1 * | 11/2005 | Bulsara ................ | A61K 9/0075 424/46 |
| 2008/0254114 A1 | 10/2008 | Jenkins et al. | |
| 2009/0317476 A1 * | 12/2009 | Robinson ............... | A61K 31/47 424/489 |

FOREIGN PATENT DOCUMENTS

| | | | |
|---|---|---|---|
| JP | 2008533174 A | 8/2008 | |
| JP | 4266824 B2 | 5/2009 | |
| JP | 2011528343 A | 11/2011 | |
| JP | 2013525338 A | 6/2013 | |
| JP | 2015500268 A | 1/2015 | |
| PT | 109030 | 12/2015 | |
| WO | WO-0132163 A1 * | 5/2001 | ............. A61K 31/40 |
| WO | 2006096462 A1 | 9/2006 | |
| WO | 2006099591 A1 | 9/2006 | |
| WO | 2008126797 A1 | 10/2008 | |
| WO | 2009074666 A1 | 6/2009 | |
| WO | 2011131947 A2 | 10/2011 | |
| WO | 2015154084 A1 | 10/2015 | |
| WO | 2017103600 A1 | 6/2017 | |

OTHER PUBLICATIONS

Foreign Communication from a related application—International Preliminary Report on Patentability of International Application No. PCT/GB2016/053953 dated Apr. 6, 2018, 11 pages.

Guidance for Industry, ANDAs: Pharmaceutical Solid Polymorphism Chemistry, Manufacturing and Controls. U.S. Department of Health and Human Services Food and Drug Administration Center for Drug Evaluation and Research (CDER), Jul. 2007.

Pilcer, Gabrielle., et al., "Formulation and Characterization of Lipid-Coated Tobramycin Particles for Dry Power Inhalation," Pharmaceutical Research, May 2006, pp. 931-940, vol. 23, No. 5, Springer Science.

Walzel, Peter, "Influence of the spray method on Product Quality and Morphology in Spray Drying," Chemical Engineering Technology, 2011, pp. 1039-1048, vol. 34, No. 7, Wiley-VCH Verlag GmbH & Co. KGaA, Weinheim.s.

Foreign communication from a related application—Office Action of Japanese Patent Application No. 2018-531556 dated Aug. 11, 2020, with English machine translation, 13 pages.

* cited by examiner

FIG. 1

Zafirlukast amorphous → Suspension (+ Water) → Size reduction (Pressure/energy) → Spray drying (Atomization) → Blending (Excipient(s)) → Filling → Inhaler Intermediate outputs: Suspension (amorphous); Nanosuspension (crystalline); Respirable agglomerates of crystalline nonparticles

FIG. 2

Zafirlukast amorphous → Suspension (+ Water) → Size reduction (Pressure/energy) → Spray drying (Atomization, Excipient(s)) → Filling → Inhaler Intermediate outputs: Suspension (amorphous); Nanosuspension (crystalline); Respirable composite particles

FIG. 3

Zafirlukast amorphous → Suspension (+ Water) → Size reduction (Pressure/energy) → Spray drying (Atomization, Excipient(s)) → Blending (Excipient(s)) → Filling → Inhaler Intermediate outputs: Suspension (amorphous); Nanosuspension (crystalline); Respirable composite particles

PREPARATION OF RESPIRABLE ZAFIRLUKAST PARTICLES

CROSS REFERENCE TO RELATED APPLICATIONS

This application is a filing under 35 U.S.C. 371 of International Application No. PCT/GB2016/053953 filed Dec. 15, 2016, entitled "Preparation of Respirable Zafirlukast Particles" which claims priority to Portuguese Patent Application No. 109030 filed Dec. 15, 2015, which applications are incorporated by reference herein in their entirety.

FIELD OF INVENTION

The present invention relates generally to zafirlukast, and in particular to particle size and polymorphic form control methods involving this API. More particularly, the present invention is in the technical field of preparing zafirlukast monohydrate particles suitable for inhalation drug products, wherein control of the particle size and crystalline form is critical. The invention also relates to pharmaceutical formulations comprising the particles, and methods for preparing them, for example dry powder formulations; and to methods for their use.

BACKGROUND OF THE INVENTION

Zafirlukast is a leukotriene receptor antagonist for the maintenance treatment of asthma, currently marketed as an oral solid dosage form, often used in conjunction with other inhaled therapies. Zafirlukast blocks the action of the cysteinyl leukotrienes, thus reducing constriction of the airways, build-up of mucus in the lungs and inflammation of the breathing passages.

U.S. Pat. Nos. 5,504,216, 5,482,963, 5,319,097, 5,993,859, 5,612,367, and 6,143,775 disclose several crystalline polymorphic forms of zafirlukast, namely an amorphous form, a crystalline monohydrate form and a crystalline anhydrous form. Polymorphic forms are different arrangements and/or conformations of the same molecule in the crystalline structure. These different arrangements can lead to different chemical and physical properties, including melting point, chemical reactivity, apparent solubility, dissolution rate, optical and mechanical properties, vapour pressure and density. [Guidance for Industry, ANDAs: Pharmaceutical Solid Polymorphism Chemistry, Manufacturing and Controls. U.S. Department of Health and Human Services Food and Drug Administration Center for Drug Evaluation and Research (CDER), July 2007]. These patents also refer that the monohydrate and anhydrous crystalline forms have been found to be physically stable, but with relatively poor bioavailability. On the other hand, the amorphous form is the most bioavailable, as disclosed in the patents, but also the less physically stable. Hence, U.S. Pat. Nos. 5,504,216, 5,482,963, 5,319,097, 5,993,859, 5,612,367, and 6,143,775 also describe pharmaceutical compositions comprising the amorphous form of zafirlukast and polyvinylpyrrolidone, used to stabilize zafirlukast amorphous form in order to successfully prepare solid oral dosage forms, while ensuring high bioavailability.

However, for pulmonary delivery of zafirlukast for the treatment of local diseases such as asthma and COPD, amongst others, a lower drug absorption/systemic bioavailability is a desired feature so that side-effects are reduced and safer medicines are generated. Furthermore, the crystalline monohydrate form is more stable than the amorphous form. Hence, for the development of a zafirlukast inhalation formulation, we have appreciated that methods for preparing the crystalline monohydrate form, preferably substantially free of other physical forms, to ensure appropriate control over drug properties, would be desirable.

U.S. Pat. Nos. 5,504,216, 5,482,963, 5,319,097, 5,993,859, 5,612,367, and 6,143,775 provide methods for preparing the amorphous form substantially free of other forms by heating the crystalline monohydrate form, and methods for preparing the crystalline monohydrate form substantially free of other forms by crystallization from hot aqueous acetone. Although these patents indicate that the amorphous form can convert into crystalline monohydrate form in the presence of water, no method is disclosed to ensure conversion of the amorphous to mostly crystalline monohydrate material. Moreover, the oral dosage pharmaceutical composition preparation methods include mixing amorphous zafirlukast with polyvinylpyrrolidone in water, while claiming that the amorphous form is maintained. But, in fact, exposure of the amorphous form to water is not sufficient for ensuring conversion to monohydrate. Therefore, the present inventors have realised there is still a need for methods for converting the amorphous zafirlukast form into crystalline monohydrate substantially free of other polymorphic forms, since conventional crystallization processes typically lead to amorphous zafirlukast mixed with other polymorphic forms. Finally, the above patents indicate that the amorphous form can be micronized prior to formulation without providing any insight either on the micronization methods or on the impact of these methods on the final material physical form. Overall, these patents refer to application of zafirlukast for oral dosage forms and do not provide any teaching for the preparation of zafirlukast suitable for inhalation formulations.

After processing according to the present invention, the zafirlukast particles are preferably comprised of 90% (by weight) or more of crystalline monohydrate form with a particle size suitable for inhalation drug products.

In the pulmonary drug delivery field, there are many types of inhaler devices able to deliver the active pharmaceutical ingredient (API) as a powder or liquid aerosol, namely dry powder inhalers (DPI), pressurized metered dose inhaler (pMDI) and nebulizers. For DPI and pMDI formulation, often there is the need to reduce the particle size of the active pharmaceutical ingredient (API) to a particle size typically between 1 and 5 microns in order to ensure proper deposition in the lungs and, consequently, efficacy.

In inhalation, the standard size-reduction technique has been jet milling (or similar dry media micronization methods); however, more recently, the use of size-reduction techniques where the API is suspended in an anti-solvent have gained momentum, owing to a number of advantages that are discussed in patent applications WO 2009/074666 and WO 2011/131947. There are several variations of these "wet media" based techniques including, but not exclusively, i) ball milling, ii) high-pressure homogenization, iii) microfluidization, and iv) ultrasonic homogenization. Following size-reduction, the preferential isolation step of the powder described in patent WO 2011/131947 is spray drying (the combination of size-reduction in "wet media" with spray drying was designated as wet polishing). The use of size-reduction in "wet media" with zafirlukast has been claimed in patent applications WO 2006/096462 and WO 2006/099591 for the preparation of nanosuspensions with improved solubility in water.

However, the WO 2009/074666 process considers the preparation of an initial feed suspension of crystalline drug substance; while patent WO 2011/131947 claims the maintenance of the polymorphic form of the API during processing. Surprisingly, the invention herein described considers the conversion of zafirlukast amorphous form in an aqueous suspension to mostly crystalline monohydrate during the wet milling step, as a consequence of the high energy input provided. On the other hand, WO 2006/096462 and WO 2006/099591 patents claim nanosuspension compositions of zafirlukast comprising at least one surface stabilizer, without disclosing the final physical form of zafirlukast. These patent applications also claim nanoparticulate compositions further comprising pharmaceutically acceptable excipients. In the present invention, the resulting suspension after the size-reduction step is absent of any surface stabilizer or surfactant to ensure the preparation of nanoparticles, which is a significant advantage considering the limited number of excipients approved or regarded as safe for inhalation formulations.

DESCRIPTION OF THE INVENTION

The present invention relates in particular to a method for producing zafirlukast crystalline monohydrate particles suitable for inhalation formulations comprising size-reduction of an aqueous suspension of amorphous zafirlukast starting raw material, coupled with physical form conversion, yielding nanoparticles, followed by isolation via spray drying or equivalents or variations thereof. Respirable particles can be formed during spray drying via nanoparticles agglomeration, further stabilized by residual amorphous material, or via addition of excipients to the suspension. This innovative concept ensures the preparation of less systemically bioavailable zafirlukast particles appropriate for the local treatment of respiratory diseases such as asthma or COPD.

As used herein the term "respirable" zafirlukast, or like expressions, means that the API is in a form suitable for administration to the lungs such that it may exert a pharmaceutical effect when given via inhalation. In a preferred aspect, respirable zafirlukast comprises particles having a particle size of from 1 to 5 μm.

In one aspect of the invention herein described, zafirlukast crystalline monohydrate respirable particles can be generated by agglomeration of the primary nanoparticles upon isolation of the nanosuspension by spray drying or by other similar spray-based method. Agglomeration upon spray drying was previously described by Walzel et al for an inorganic molecule, yielding particles not suitable for pulmonary delivery with a particle size above 5 μm [Influence of the spray method on Product Quality and Morphology in Spray Drying, Chemical Engineering Technology (2011), 34: 1039-1048]. The agglomerates are formed due to the cohesive nature or high surface energy of the nanoparticles. In this aspect of the present invention, the agglomerates can, if desired, be further stabilized by residual amounts of amorphous zafirlukast glass connecting the nanoparticles, not requiring any additional excipients as described in patents WO 2006/096462 and WO 2006/099591 or Pilcer et al. [Formulation and characterization of lipid-coated tobramycin particles for dry powder inhalation, Pharmaceutical Research (2006), 23: 931-940]. Nevertheless, the present invention does not exclude the use of excipients as bulking agents, glass formers or stabilizers to further stabilize the zafirlukast nanoparticles into respirable particles. The final particle size is controlled in the spray drying step by controlling the spray droplet size, as will be understood by those skilled in this field.

Figure 1:
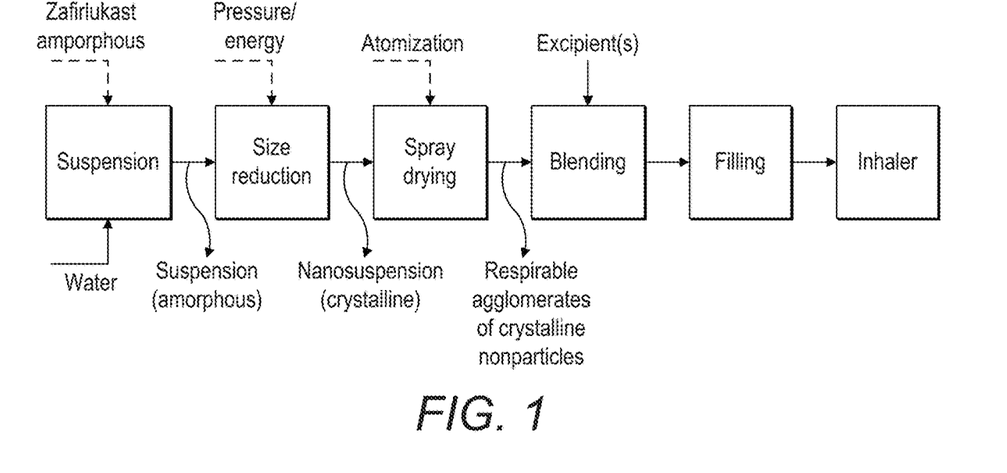
FIG. 1: Scheme of the method steps leading to the zafirlukast crystalline monohydrate agglomerates, used in carrier-based DPI formulations.

In another aspect of the invention, a pharmaceutical composition of respirable and stable zafirlukast agglomerates, with a particle size of from 1 to 5 μm and carriers, preferably coarse carriers, suitable for pulmonary delivery via a dry powder inhaler device is disclosed (carrier-based DPI formulation)—FIG. 1. For such agglomerates, or composites, the particle size is the mean particle size diameter as measured by a suitable technique (for example, laser diffraction, scanning electron microscopy, or light microscopy, as is conventional in the art) based on transformation to a spherical particle. The carriers are required to improve the aerodynamic performance and allow successful metering and dosing of the zafirlukast agglomerates, considering that typical API doses for pulmonary delivery are in the microgram range.

In another aspect of the invention, a pharmaceutical composition is disclosed wherein water soluble excipients with inhalation precedence, such as sugars, amino acids, salts or polymers, can be added at the end of the size-reduction in "wet-media" step, yielding composite particles of zafirlukast nanoparticles in an excipient matrix after spray drying, with a particle size between 1 to 5 μm, which are suitable for pulmonary delivery via a dry powder inhaler device (carrier-free composite particles DPI formulation). The composite particles eliminate the need for additional formulation steps to prepare a final inhalation formulation, yielding a carrier-free pharmaceutical composition—FIG. 2.

Figure 3:
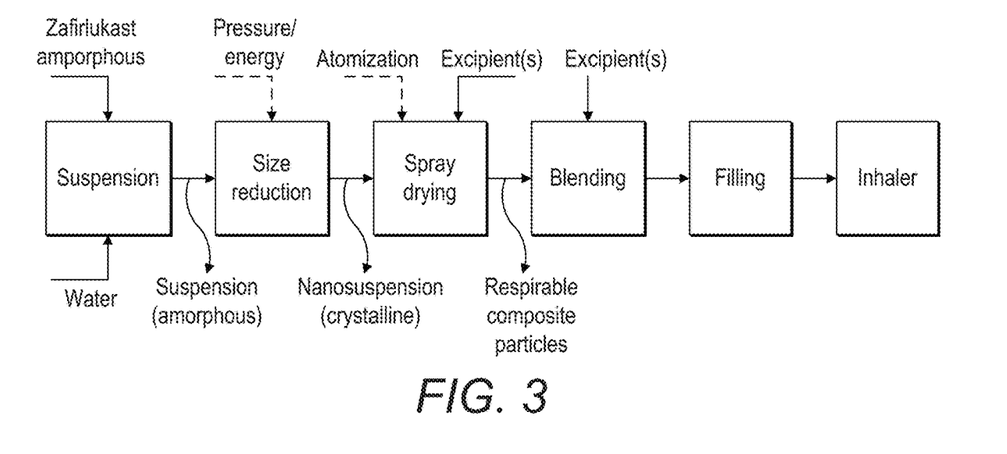
FIG. 3: Scheme of the method steps leading to zafirlukast crystalline monohydrate composite particles, used in carrier-based composite particles DPI formulations.

In another aspect of the invention, a pharmaceutical composition is disclosed wherein the respirable composite particles of zafirlukast nanoparticles are further blended with carriers, such as coarse carriers, to yield a formulation suitable for pulmonary delivery via a dry powder inhaler device (carrier-based composite particles DPI formulation)—FIG. 3. This formulation eliminates the need for partially amorphous zafirlukast to further stabilize the agglomerates of crystalline zafirlukast nanoparticles which is normally used in the carrier-based composition.

The invention herein disclosed minimises or overcomes the shortcomings identified in the art, by i) specifically addressing the problem of generating in a controlled way zafirlukast crystalline monohydrate particles from an amorphous starting raw material and ii) in enabling the preparation of respirable zafirlukast particles suitable for preparing inhalation formulations for the local treatment of respiratory diseases such as asthma.

According to one aspect of the present invention, there is provided a method for the preparation of respirable zafirlukast monohydrate particles comprising the steps of:

a. Preparation of an aqueous suspension of amorphous zafirlukast;
b. Size-reduction with conversion of the suspended zafirlukast into crystalline monohydrate nanoparticles;
c. Isolation of the crystalline zafirlukast in the form of a dry powder.

The powder may, for example, be isolated by spray drying or by an equivalent process which is suitable to form a dry powder, such as spray freeze drying or supercritical fluid assisted extraction or drying.

The isolated powder may be formulated into a pharmaceutical composition, either with or without additional excipients or carriers. A preferred formulation is one suitable for a DPI.

The size-reduction step preferably comprises a wet media based technique. More preferably, a high energy input technique is used, such as microfluidisation, high-pressure homogenization, ball milling, or ultrasonic homogenization, and the skilled person will be aware of how these techniques may be employed.

In a preferred aspect, after step (c) at least 90% (by weight) of the zafirlukast present is in the form of crystalline zafirlukast monohydrate.

In a preferred aspect, after step (c) the particles have a particle size of from 1 to 5 μm. Preferably, the said particles comprise agglomerates of zafirlukast nanoparticles, although this is not essential.

In a preferred aspect, one or more pharmaceutically acceptable excipients may be added prior to the step of isolation of the crystalline zafirlukast. Preferably, the step of isolation then comprises spray drying, although any suitable equivalent may be used. In this way, it is possible to isolate composite particles which comprise, within each particle, both crystalline zafirlukast monohydrate and one or more of the chosen excipients.

In a preferred aspect, the one or more excipients added prior to the step of isolation of the crystalline zafirlukast are chosen from sugars, amino acids, salts, polymers or mixtures of any one or more thereof. Preferably, the one or more excipients comprise trehalose, mannitol, leucine or mixtures of any one or more thereof.

In a preferred aspect, in the method of the invention up to and including step (b) (that is, the size reduction step), the process does not comprise use of any surfactant, surface stabilizer or surface active agent. The method of the invention may, if desired, also not comprise use of any surfactant, surface stabilizer or surface active agent in step (c), and/or in any subsequent step, although often it is preferred to include excipients in step (c) but not before.

In particular, in a preferred aspect, in the method of the invention up to and including step (b) (that is, the size reduction step), and, if desired, also in step (c), and/or in any subsequent step, the process does not comprise use of any one or more of the following compounds: povidone, copovidone, hydroxypropylmethylcellulose (HPMC), polyoxyethylene sorbitan fatty acid ester, poloxamer, polyvinylpyrrolidone (PVP) or tyloxapol.

In a related aspect, the process of the invention allows the production of novel particles comprising zafirlukast, in particular particles which are suitable for administration by inhalation. This, in another aspect, the invention provides zafirlukast respirable particles characterized by comprising crystalline monohydrate zafirlukast.

Zafirlukast respirable particles according to the invention preferably are characterized in that at least 90% (by weight) of the zafirlukast present is in the form of crystalline zafirlukast monohydrate.

Preferably, zafirlukast respirable particles according to the invention comprise a particle size of from about 1 to about 5 μm.

In one preferred aspect, zafirlukast respirable particles according to the invention comprise agglomerates of nanoparticles of zafirlukast.

In one aspect, the zafirlukast respirable particles according to the invention may comprise one or more excipients. The one or more excipients may, for example, be chosen from sugars, amino acids, salts, polymers or mixtures of any one or more thereof.

The invention also provides zafirlukast respirable particles obtainable, or obtained by, a process according to the invention described herein.

In a further aspect, the invention provides a pharmaceutical composition comprising zafirlukast respirable particles according to the invention. If desired, the composition does not comprise any corticosteroid. In one aspect, if desired, any composition comprising the zafirlukast respirable particles according to the invention does not comprise any surfactant, surface stabilizer or surface active agent. In particular, if desired, any composition comprising the zafirlukast respirable particles according to the invention does not comprise any one or more of the following compounds: povidone, copovidone, hydroxypropylmethylcellulose (HPMC), polyoxyethylene sorbitan fatty acid ester, poloxamer, polyvinylpyrrolidone (PVP) or tyloxapol. However, in certain compositions, one or more of these compounds may be included, depending largely upon the type of composition in question.

Such a pharmaceutical composition may, for example, be for a dry powder inhaler and further comprise a carrier. Suitable carriers will be known to those in the DPI formulation field. For example, the carrier may comprise a monosaccharide. Preferably, the carrier comprises lactose or lactose monohydrate.

The invention also provides the use of zafirlukast respirable particles according to the invention, or the use of a pharmaceutical composition according to the invention, for the treatment of respiratory diseases, such as asthma or COPD.

The invention also provides zafirlukast respirable particles according to the invention, or a pharmaceutical composition according to the invention, for use in medicine. The use in medicine may, for example, be for use in the treatment of respiratory diseases such as asthma or COPD.

DETAILED DESCRIPTION OF THE INVENTION

Preferred features of the invention are described in more detail below.
  a) The invention comprises the preparation of an initial aqueous suspension of amorphous zafirlukast, in which water is the anti-solvent. As used herein, the term "amorphous zafirlukast" is defined as zafirlukast starting raw material wherein at least 70% (by weight) of the zafirlukast is in the amorphous state.

b) The invention comprises a size-reduction step in wet media as a means to size-reduce and convert the suspended amorphous zafirlukast into crystalline monohydrate nanoparticles, preferably by means of high energy input. The zafirlukast nanoparticles are typically characterized by a size below about 1000 nm. As used herein, the term "particle size" is defined as the value below which 50% of the volume of the material exists. In the size-reduction step, the suspension is comminuted mostly by particle-particle collisions, shear forces and solvent cavitation, providing energy to support crystallization.

c) The invention suitably makes use of a spray drying apparatus, or equivalents or variations thereof, to isolate the nanoparticles as a dry powder. In a conventional spray-drying process, the liquid suspension is atomized into droplets. When these droplets enter the drying chamber, along with a stream of drying gas, the droplets suffer a flash evaporation, in which the anti-solvent is removed from the particles surface. The powder formed is afterwards moved into a cyclone where the particles in contact with centrifugal forces are collected or moved to a collecting filter bag. For a person skilled in the art, equivalents or variations of conventional spray drying comprise any method in which the suspension is atomized into droplets and the anti-solvent removed by mechanisms other than evaporation, namely sublimation, extraction, or adsorption. Examples of these variations include spray freeze drying or supercritical fluid assisted extraction or drying.

d) The invention preferably comprises the formation of agglomerates in the particle size range of from about 1 to about 5 μm of zafirlukast monohydrate primary nanoparticles upon spray drying. The formation and stabilization of the agglomerates is due to the high cohesivity (surface energy) of the nanoparticles being isolated as well as additional contribution of residual amounts of solubilized zafirlukast forming an amorphous glass connecting the nanoparticles upon spray drying. The final particle size may be controlled via spray drying parameters, as will be understood by those skilled in the art.

e) The invention may comprise the addition of pharmaceutically acceptable excipients prior to spray drying (or an equivalent process) to generate composite particles in the size range of from about 1 to about 5 μm of zafirlukast crystalline monohydrate with excipients such as sugars, amino acids, salts and polymers. The final particle size is controlled via spray drying parameters. The excipients may be used as glass formers or bulking agents for the preparation of zafirlukast composite particles with increased storage stability. Preferable excipients include, but are not limited to, lactose, trehalose, sucrose, raffinose, mannitol, glycine, leucine, sodium chloride, calcium chloride, magnesium chloride and biodegradable polymers such as poly-lactic acid, poly-lactic-glycolic-acid, poly lysine, and hyaluronic acid.

f) The invention encompasses pharmaceutical compositions comprising the prepared zafirlukast crystalline monohydrate agglomerates and carriers with inhalation relevance, typically lactose monohydrate, for a DPI.

g) The invention also provides a pharmaceutical composition comprising composite particles of zafirlukast crystalline monohydrate and one or more pharmaceutically acceptable excipients, suitable for use in a DPI.

h) The invention also provides a pharmaceutical composition comprising the prepared composite particles of zafirlukast crystalline monohydrate and carriers suitable for inhalation, typically lactose monohydrate, suitable for use in a DPI.

The main advantages of the present invention includes the preparation of physically stable and less systemically bioavailable zafirlukast crystalline monohydrate particles suitable for inhalation formulations, while coupling particle engineering and polymorphic form conversion methods, ensuring control over the API properties. These particulates can be used, for example, in DPI carrier-based formulations. In addition, carrier-free DPI formulations of crystalline zafirlukast may be prepared through the method of the invention, circumventing the challenges of ensuring homogeneity and low efficiency associated with carrier-based DPI formulations while enabling aerodynamic performance independent of the relative content of API in the excipient matrix.

EXAMPLES

The following examples are illustrative only and do not restrict the scope of the invention.

Example 1

This example demonstrates the successful formation of zafirlukast crystalline monohydrate particulates with a particle size in the inhalation range via the present invention. A comparative example is also shown to illustrate that physical form conversion only occurs by providing a high energy input during the size-reduction step in aqueous media.

Figure 4:
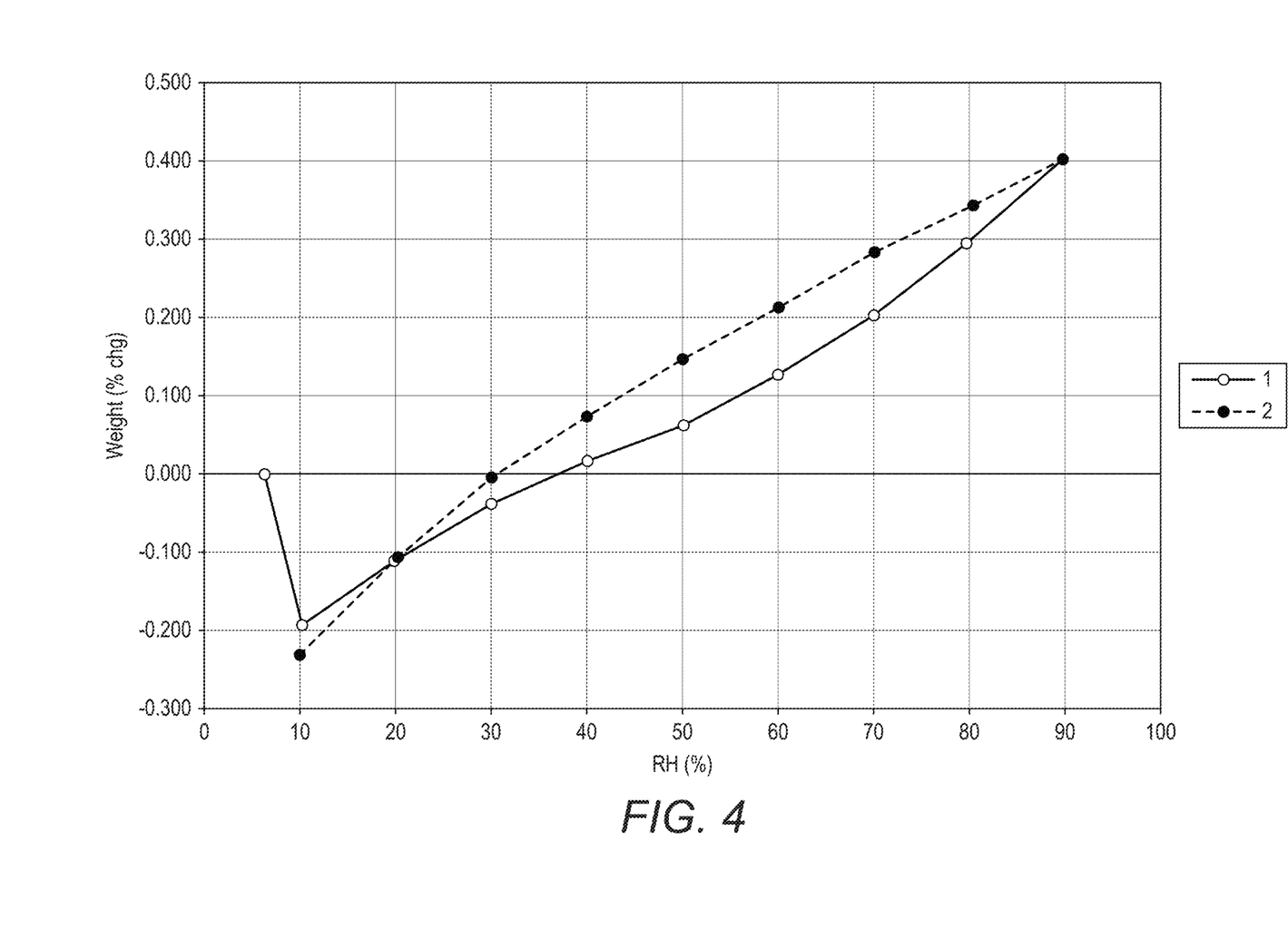
FIG. 4: DVS profile of amorphous zafirlukast, generated by spray drying from an acetone solution: (1) adsorption and (2) desorption.

One feed solution was prepared by dissolving amorphous zafirlukast in acetone at a total solids concentration of 5% w/w. The solution was spray dried in a laboratory scale spray dryer (BUCHI model B-290 Advanced) under the operating conditions summarized in the table below (trial #1). The dynamic vapour sorption (DVS) profile indicates that the amorphous material is not very hygroscopic and that no solid state conversions occur during the analysis as the sorption and desorption curves are similar—FIG. 4. Hence the amorphous form cannot convert to crystalline monohydrate by exposure to environmental conditions.

One feed mixture was prepared by suspending coarse amorphous zafirlukast in water with total solids concentration of 2.6% w/w and was processed using a high shear mixer at 8,000 rpm (trial #2), followed by drying in an oven. The X-ray powder diffraction (XRPD) diffractogram was similar to the pattern ascribed to crystalline monohydrate, but an amorphous halo could still be observed—FIG. 5.

The thermogravimetric analysis (TGA) has shown a decrease in weight of 1.8% w/w at ~129° C. (theoretical amount of water for crystalline monohydrate is 3.0% w/w); thus confirming that the final solid is a mixture of amorphous and crystalline monohydrate zafirlukast with only about 60% of crystalline monohydrate form present (as estimated by the ratio between the water content by TGA of the spray dried powders and the theoretical water content for the monohydrate form).

Three feed mixtures were prepared by suspending coarse amorphous zafirlukast in water with total solids concentration of 5% w/w and were processed by microfluidization (Microfluidics model M110-EH30), a size-reduction technique with higher energy input than high shear mixing, followed by drying in a laboratory scale spray dryer (BUCHI model B-290 Advanced). The operating conditions are summarized in the table below trials—#3 to #5. The particle size of the final suspension and spray dried powder was determined by laser diffraction wet method (expressed as particle size below which 50% of the volume of material exists).

Figure 6:
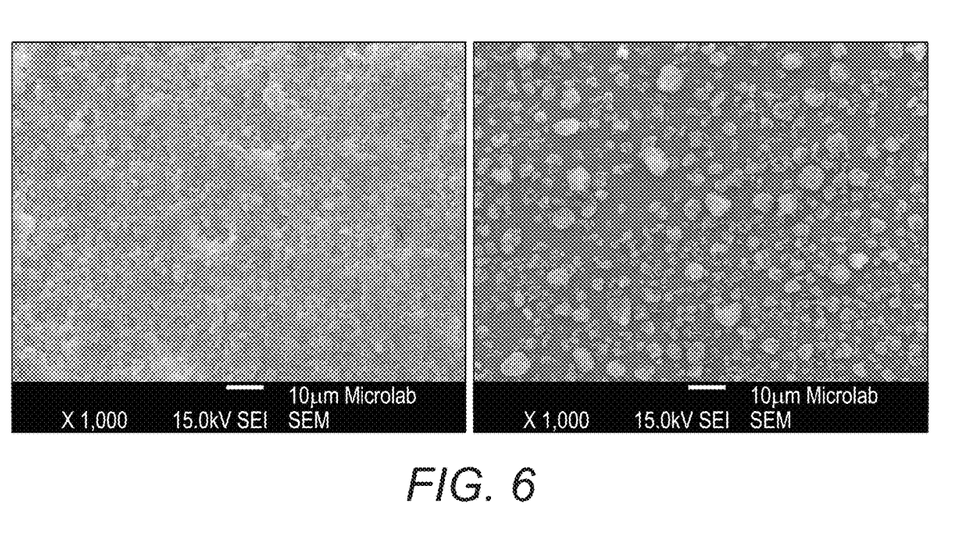
FIG. 6: SEM micrographs of zafirlukast crystalline monohydrate (A) after size reduction in wet media and (B) after spray drying.

The particle size obtained after microfluidization of trials #3 to #5 indicates that a nanosuspension is obtained, which is further confirmed by the scanning electron microscopy (SEM) micrographs of the drop cast suspension in FIG. 6.

Figure 5:
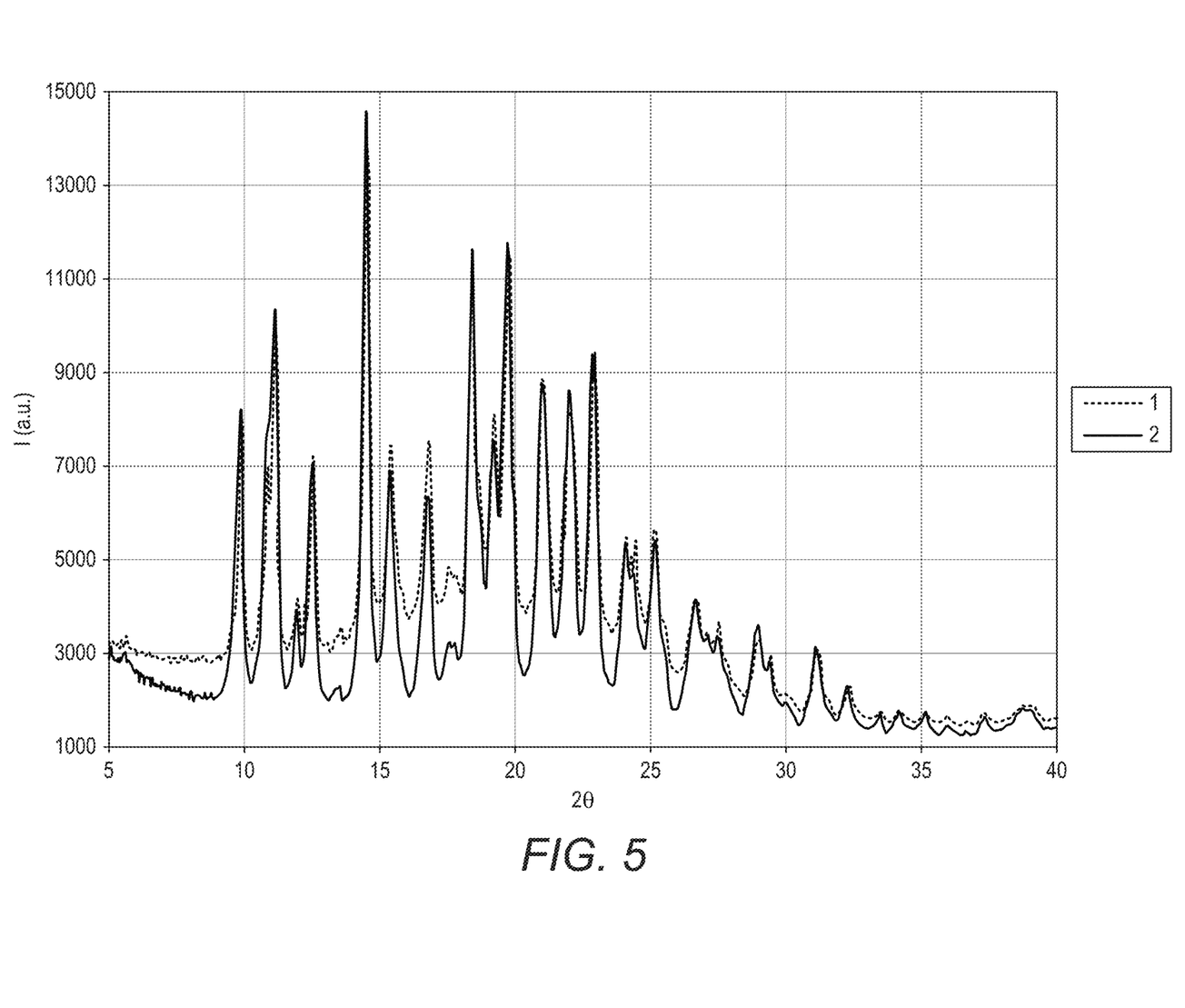
FIG. 5: (1) XRPD diffractogram of zafirlukast crystalline monohydrate after low-energy wet milling (high shear mixing) and (2) XRPD diffractogram of zafirlukast crystalline monohydrate after high-energy wet milling (microfluidization).

After spray drying, the XRPD diffractograms for trials #3 to #5 indicated the presence of mostly crystalline monohydrate form, as shown in FIG. 5 for trial #3. The TGA analysis for the trials have yielded a water content above 2.7% w/w for the zafirlukast spray dried powders, which indicates that at least more than 90% of crystalline monohydrate material was obtained. The final particle size was within the typical respirable range of 1 to 5 µm, indicating that agglomeration of the primary nanoparticles has occurred. This observation was further confirmed by the SEM analysis of the powder, as shown in FIG. 6.

as assessed by high pressure liquid chromatography (HPLC). Capsules were filled with 15 mg for supporting aerodynamic performance characterization by Next Generation Impactor (NGI) at 4 kPa pressure drop. The results are summarized in the table below for trials #1 to #3.

The NGI results indicate that a DPI carrier-based formulation using zafirlukast monohydrate particulates is feasible in achieving an aerodynamic performance compliant with delivery to the lungs, as a mass median aerodynamic diameter (MMAD) below 5 µm was successfully obtained.

|  |  | Trial | | |
|---|---|---|---|---|
|  |  | #1 | #2 | #3 |
|  | Blending | | | |
| Zafirlukast particulates | % | 1.67 | 1.67 | 1.67 |
| Fine lactose | % | 5.00 | 10.00 | 5.00 |

| | | Trial | | | | |
|---|---|---|---|---|---|---|
| | | #1 | #2 | #3 | #4 | #5 |
| | | | Wet milling | | | |
| Equipment | — | SD | High shear mixing + Drying | Microfluidization + SD | Microfluidization + SD | Microfluidization + SD |
| Nr of cycles | — | N.AP. | N.AP. | 50 | 50 | 50 |
| Pressure | bar | N.AP. | N.AP: | 750 | 750 | 750 |
| Particle size | µm | N.AP. | N.AP. | 0.3 | 0.3 | 0.4 |
| | | | Spray drying | | | |
| Rotameter | mm | 50 | N.AP. | 30 | 60 | 60 |
| T_in | ° C. | 153 | N.AP. | 69 | 77 | 81 |
| T_out | ° C. | 120 | N.AP. | 45 | 45 | 45 |
| Water content by TGA | % w/w | N.AP. | 1.8 | 2.7 | 2.9 | 3.0 |
| XRPD | — | Amorphous | Crystalline monohydrate/Amorphous | Crystalline monohydrate | Crystalline monohydrate | Crystalline monohydrate |
| Crystalline monohydrate content | — | N.D. | 60 | 90 | 95 | 98 |
| Particle size | µm | N.AP. | N.AP. | 4.5 | 3.5 | 3.2 |

Note:
T_in—inlet drying temperature;
T_out—outlet drying temperature;
N.AP.—Not applicable;
N.D.—not detected.

Hence, these results demonstrate that the present invention is able to fulfill all the previous aims and goals of obtaining respirable particles of zafirlukast crystalline monohydrate.

Example 2

This example demonstrates successful formulation of zafirlukast crystalline monohydrate particulates prepared as described beforehand (Example 1) in a lactose ternary mixture to support aerodynamic performance evaluation with two capsule-based inhalers: Hovione prototype inhaler and PlastiApe commercial inhaler—carrier-based DPI formulation as illustrated in FIG. 1.

The ternary lactose-based formulation was prepared by geometric dilution of zafirlukast crystalline monohydrate agglomerates at 1.67% w/w using a low-shear Turbula mixer (Glen Mills). The final blend was shown to be homogeneous, -continued

|  |  | Trial | | |
|---|---|---|---|---|
|  |  | #1 | #2 | #3 |
| Coarse lactose | % | 93.33 | 93.33 | 93.33 |
| Assay; RSD | % | 95; 1 | 95; 2 | 95; 1 |
| | Aerodynamic performance by NGI | | | |
| Device | — | Hovione | Hovione | PlastiApe |
| Flow | L/min | 40 | 40 | 40 |
| ED | % | 67 | 59 | 92 |
| $FPF_{ED}$ | % w/w | 17 | 20 | 22 |
| MMAD | µm | 2.8 | 2.0 | 3.2 |

Note:
RSD—residual standard deviation of the blend assay; ED—emitted dose; $FPF_{ED}$—Fine particle fraction of the emitted dose; MMAD—mass median aerodynamic diameters.

Hence, the results demonstrate that the present invention can be used for preparing zafirlukast crystalline monohydrate pharmaceutical compositions for DPI.

Example 3

Figure 2:
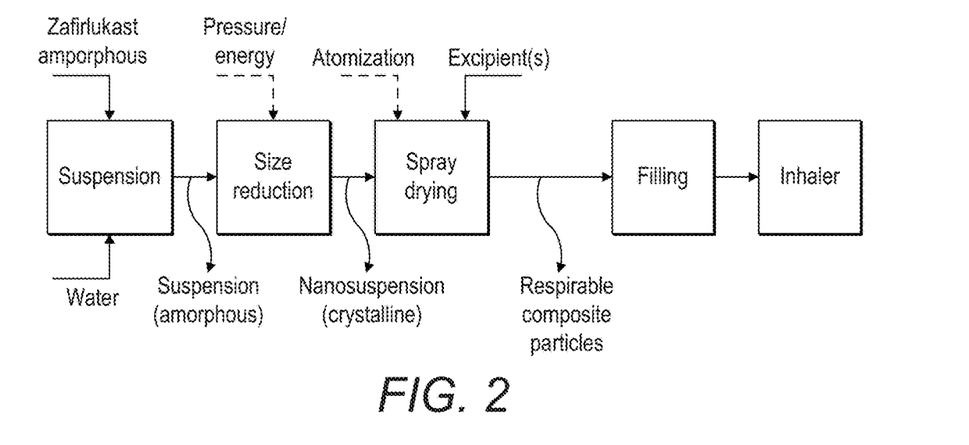
FIG. 2: Scheme of the method steps leading to zafirlukast crystalline monohydrate composite particles, used in carrier-free DPI formulation.

This example demonstrates successful preparation of zafirlukast crystalline monohydrate composite particles that can directly support a DPI pharmaceutical composition without the need of further blending/mixing steps with carriers—carrier-free DPI formulation as illustrated in FIG. 2. The composite particles aerodynamic performance was evaluated with one capsule-based inhaler from Plastiape.

Composite particles were generated by dissolving mannitol as an excipient in an aqueous suspension of the crystalline zafirlukast nanoparticles obtained after the size-reduction step (detailed in Example 1), at different ratios of mannitol and zafirlukast crystalline monohydrate nanoparticles—trials #1 and #2. Other composite particles were prepared by dissolving trehalose and leucine as excipients—trial #3. All resulting feed suspensions were spray dried in a laboratory scale spray dryer (BUCHI model B-290 Advanced). The spray dried powders were characterized in terms of particle size by laser diffraction and XRPD. The aerodynamic performance was evaluated using a Fast Screening Impactor (FSI), as detailed in the table below.

Figure 7:
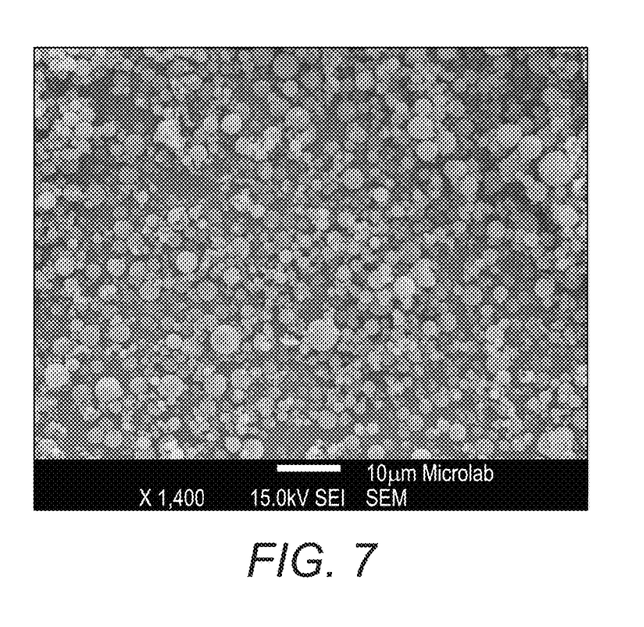
FIG. 7: SEM micrographs of zafirlukast crystalline monohydrate composite particles with mannitol after spray drying.

Well-defined particles with a size in agreement with the 1 to 5 μm respirable range were obtained, as shown by laser diffraction and the SEM micrographs in FIG. 7. The XRPD diffractogram of trial #1 and #2 have shown the presence of crystalline mannitol (mixture of polymorph forms α and β). On the other hand, when using trehalose and leucine as excipients, the XRPD indicates the presence of amorphous trehalose and crystalline peaks of leucine. The FSI results indicate that a DPI composite particles formulation using zafirlukast monohydrate agglomerates is feasible in achieving an aerodynamic performance compliant with delivery to the lungs: fine particle fractions over the emitted dose (FPF$_{ED}$) above 50% were obtained.

|  |  | Trial | | |
| --- | --- | --- | --- | --- |
|  |  | #1 | #2 | #3 |
| Composition of the spray dried powder | | | | |
| Zafirlukast particulates | % | 1.0 | 10.0 | 1.0 |
| Mannitol | % | 99.0 | 90.0 | 0 |
| Trehalose | % | 0 | 0 | 79.5 |
| Leucine | % | 0 | 0 | 19.5 |
| Spray drying | | | | |
| C_solids | % w/w | 5 | 5 | 2 |
| Rotameter | mm | 60 | 60 | 60 |
| T_in | ° C. | 117 | 117 | 132 |
| T_out | ° C. | 80 | 80 | 95 |
| XRPD | — | Crystalline | Crystalline | Crystalline/Amorphous |
| PS | μm | 1.5 | 1.5 | 1.2 |
| Aerodynamic performance by FSI | | | | |
| Device | — | PlastiApe | PlastiApe | PlastiApe |
| Flow | L/min | 40 | 40 | 60 |
| ED | % | 93 | 89 | 100 |
| FPF$_{ED}$ | % w/w | 58 | 56 | 70 |

Note:
T_in—inlet drying temperature; T_out—outlet drying temperature; C_solids—concentration of total solids dissolved/suspended; ED—emitted dose; FPF$_{ED}$—Fine particle fraction of the emitted dose.

Hence, the results demonstrate that the present invention can be used for preparing zafirlukast crystalline monohydrate composite particles as carrier-free pharmaceutical compositions for DPI.

Example 4

This example demonstrates successful formulation of zafirlukast crystalline monohydrate composite particles in a lactose ternary mixture to support aerodynamic performance evaluation with one capsule-based inhaler: Hovione prototype inhaler—carrier-based composite particles DPI formulation as illustrated in FIG. 3.

Composite particles were produced by dissolving mannitol in an aqueous suspension of the crystalline zafirlukast nanoparticles obtained after the size-reduction step (detailed in Example 1) according to the ratios in the table below trial—#1. The feed suspension was spray dried in a laboratory scale spray dryer (BUCHI model B-290 Advanced), yielding well-defined particles with a size in agreement with the 1 to 5 μm respirable range. The XRPD diffractogram has shown the presence of fully crystalline material in agreement with Example 3.

The ternary lactose-based formulation was prepared by geometric dilution of the mannitol-based zafirlukast crystalline monohydrate composite particles at 5.0% w/w using a low-shear Turbula mixer (Glen Mills). The final blend was shown to be homogeneous, as assessed by HPLC. Capsules were filled with 15 mg for supporting aerodynamic performance characterization by NGI at 4 kPa pressure drop. The results are summarized in the table below.

|  |  | Trial #1 |
| --- | --- | --- |
| Composition of the spray dried powder | | |
| Zafirlukast nanoparticles | % | 22.0 |
| Mannitol | % | 78.0 |
| Spray drying | | |
| C_solids | % w/w | 5 |
| Rotameter | mm | 60 |
| T_in | ° C. | 116 |
| T_out | ° C. | 80 |
| XRPD | — | Crystalline |
| Blending | | |
| Zafirlukast composite particles | % | 5.0 |
| Fine lactose | % | 5.0 |
| Coarse lactose | % | 90.0 |
| Assay; RSD | % | 95; 4 |
| Aerodynamic performance by NGI | | |
| Device | — | Hovione |
| Flow | L/min | 40 |
| ED | % | 46 |
| FPF$_{ED}$ | % w/w | 33 |
| MMAD | μm | 3.6 |

Note:
T_in—inlet drying temperature; T_out—outlet drying temperature; C_solids—concentration of total solids dissolved/suspended; RSD—residual standard deviation of the blend assay; ED—emitted dose; FPF$_{ED}$—Fine particle fraction of the emitted dose; MMAD—mass median aerodynamic diameters.

The NGI results indicate that a DPI carrier-based formulation using zafirlukast monohydrate composite particles is feasible in achieving an aerodynamic performance compliant with delivery to the lungs, as a MMAD below 5 μm was successfully obtained.

Hence, the results demonstrate that the present invention can be used for preparing zafirlukast crystalline monohydrate composite particles as carrier-based pharmaceutical compositions for DPI.

The invention claimed is:

1. A method for the preparation of respirable zafirlukast monohydrate particles comprising the steps of:
   a. preparation of an aqueous suspension of amorphous zafirlukast;
   b. size-reduction with conversion of the suspended zafirlukast into crystalline monohydrate nanoparticles;
   c. isolation of the crystalline zafirlukast in the form of a dry powder;
   wherein the size-reduction step comprises a high energy input technique.

2. The method according to claim 1 wherein the powder is isolated by spray drying or by an equivalent process which is suitable to form a dry powder.

3. The method according to claim 1 wherein after step (c) at least 90% (by weight) of the zafirlukast present is in the form of crystalline zafirlukast monohydrate.

4. The method according to claim 1 wherein after step (c) the particles have a particle size of from 1 to 5 µm.

5. The method according to claim 4 wherein said particles comprise agglomerates of zafirlukast nanoparticles.

6. The method according to claim 1 wherein one or more pharmaceutically acceptable excipients are added prior to the step of isolation of the crystalline zafirlukast.

7. The method according to claim 6 wherein the step of isolation comprises spray drying.

8. The method according to claim 6 wherein the one or more excipients are chosen from sugars, amino acids, salts, polymers or mixtures.

9. The method according to claim 8 wherein the one or more excipients comprise trehalose, mannitol, leucine or mixtures thereof.

10. The method according to claim 1 wherein up to and including step (b) the process does not comprise use of any surfactant, surface stabilizer or surface active agent.

11. Zafirlukast respirable particles characterized by comprising crystalline monohydrate zafirlukast.

12. Zafirlukast respirable particles according to claim 11 wherein at least 90% (by weight) of the zafirlukast present is in the form of crystalline zafirlukast monohydrate.

13. Zafirlukast respirable particles according to claim 11 wherein the particle size is from 1 to 5 µm.

14. Zafirlukast respirable particles according to claim 11 wherein the particles comprise agglomerates of nanoparticles.

15. Zafirlukast respirable particles according to claim 11 wherein the particles comprise one or more excipients.

16. Zafirlukast respirable particles according to claim 15 where the one or more excipients are chosen from sugars, amino acids, salts, polymers or mixtures of any one or more thereof.

17. Zafirlukast respirable particles obtainable according to the process of claim 1.

18. A pharmaceutical composition comprising particles according to claim 11.

19. The pharmaceutical composition according to claim 18 for a dry powder inhaler further comprising a carrier.

20. The pharmaceutical composition according to claim 19 wherein the carrier comprises a monosaccharide.

21. The pharmaceutical composition according to claim 20 wherein the carrier comprises lactose or lactose monohydrate.

22. A method comprising administering to a subject in need thereof the zafirlukast respirable particles according to claim 11, or the pharmaceutical composition comprising crystalline monohydrate zafirlukast according to claim 11 for the treatment of respiratory diseases.

23. The method according to claim 22 where the respiratory disease is asthma or COPD.

24. A method comprising utilizing the zafirlukast respirable particles according to claim 11, or the pharmaceutical composition comprising crystalline monohydrate zafirlukast according to claim 11 in medicine.

25. The method of claim 1, wherein the high energy input technique comprises microfluidisation, high-pressure homogenization, ball milling, or ultrasonic homogenization.

26. The method of claim 2, wherein the equivalent process which is suitable to form a dry powder comprises spray freeze drying or supercritical fluid assisted extraction or drying.

* * * * *

UNITED STATES PATENT AND TRADEMARK OFFICE
CERTIFICATE OF CORRECTION

PATENT NO. : 10,987,305 B2
APPLICATION NO. : 16/062766
DATED : April 27, 2021
INVENTOR(S) : Eunice Costa et al.

Page 1 of 1

It is certified that error appears in the above-identified patent and that said Letters Patent is hereby corrected as shown below:

On the Title Page

Item (73) replace "Assignee: Cipla Limited, Mumbai (IN)" with --Hovione Scientia Limited, Cork (IE)--.

In the Claims

Claim 8, Column 13, Line 29, replace "polymers or mixtures" with --polymers or mixtures thereof--.

Signed and Sealed this
Thirty-first Day of August, 2021

Drew Hirshfeld
*Performing the Functions and Duties of the*
*Under Secretary of Commerce for Intellectual Property and*
*Director of the United States Patent and Trademark Office*